United States Patent [19]

Jensen

[11] Patent Number: 4,901,714
[45] Date of Patent: Feb. 20, 1990

[54] BANDAGE

[75] Inventor: Ole R. Jensen, River Vale, N.J.

[73] Assignee: E. R. Squibb & Sons, Inc., Princeton, N.J.

[21] Appl. No.: 242,179

[22] Filed: Sep. 9, 1988

[51] Int. Cl.$^4$ ............................................. H61L 15/00
[52] U.S. Cl. .................................... 128/156; 128/155;
   128/163; 128/165; 128/846; 128/847; 128/857;
   128/858; 128/889; 128/890; 128/893; 128/894
[58] Field of Search ............... 128/156, 155, 163, 165,
   128/847, 858, 888–890, 893, 894; 604/358, 368,
   369

[56] References Cited
U.S. PATENT DOCUMENTS

| 3,092,103 | 6/1963 | Mower | 128/858 |
|---|---|---|---|
| 4,240,416 | 12/1980 | Boich | 604/378 |
| 4,297,995 | 11/1981 | Golub | 128/156 |
| 4,499,896 | 2/1985 | Heinecke | 128/156 |
| 4,564,010 | 1/1986 | Coughlan et al. | 128/156 |
| 4,786,282 | 11/1988 | Wagle et al. | 128/156 X |
| 4,793,003 | 12/1988 | Riedel et al. | 128/858 |

Primary Examiner—Richard J. Apley
Assistant Examiner—N. Paul
Attorney, Agent, or Firm—James & Franklin

[57] ABSTRACT

A layer of plastic, either in film or coating form, is bonded to a sheet of non-woven material to form a base. When film is used, it is preferably smaller in size than the non-woven material and affixed to the top surface thereof by an acrylic adhesive. The plastic film is coated, on its exposed surface, with a layer of acrylic adhesive. When the plastic is in the form of a coating, it is bonded to the bottom surface of the non-woven material. A superabsorbent pad, smaller in size than the base, is wrapped in non-woven material and affixed to the base by the exposed adhesive layer. The remaining portion of the exposed adhesive layer forms a border around the superabsorbent pad for adhering the bandage to the skin.

5 Claims, 4 Drawing Sheets

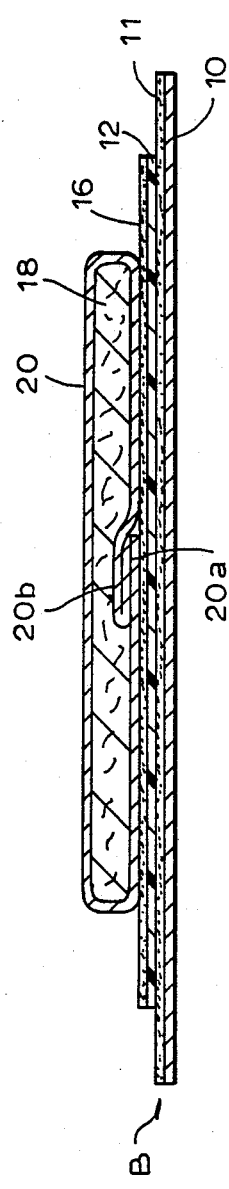
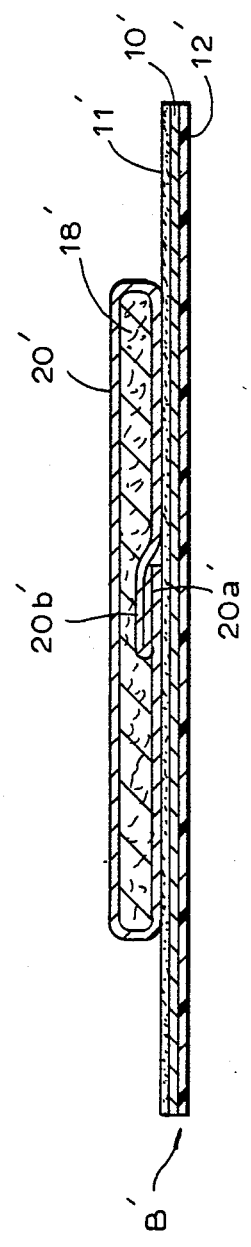

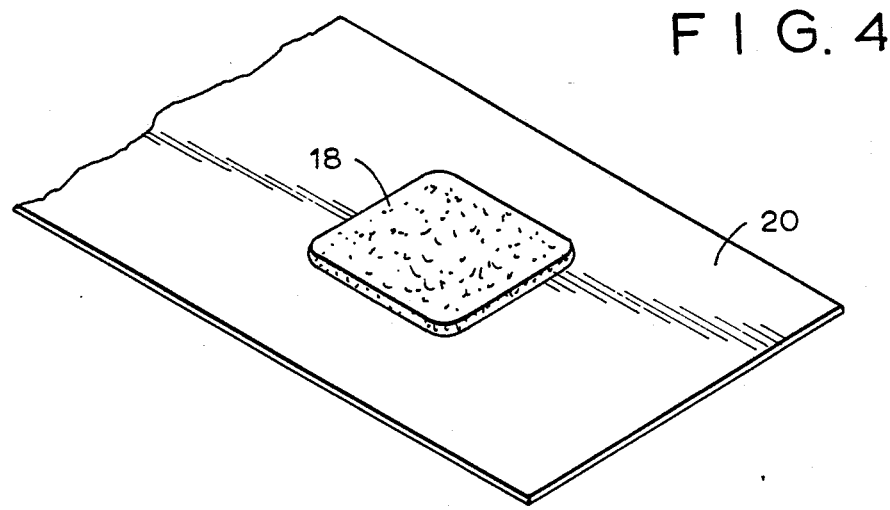
FIG. 4
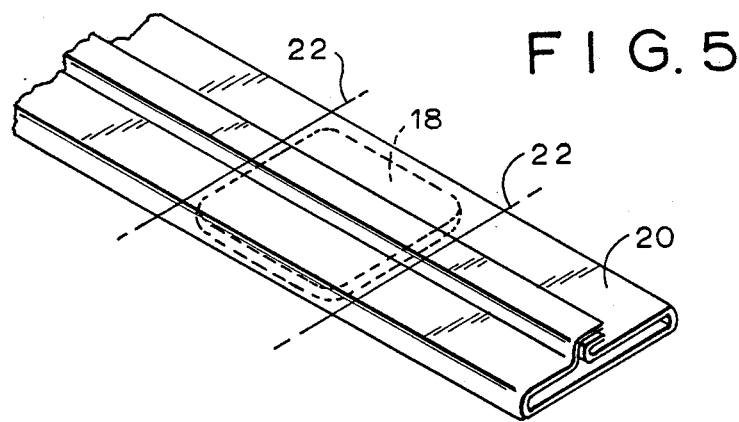
FIG. 5
FIG. 6
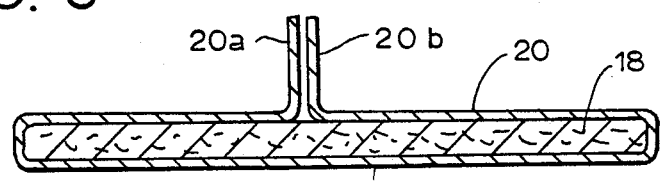
FIG. 7
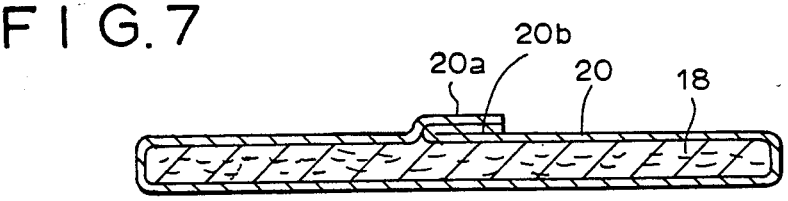

BANDAGE

The present invention relates to bandages and more particularly to an improved bandage structure which has superior absorbency and retention properties and demonstrates the ability to adhere tightly to the skin even as it is flexed.

Post operative ileostomy and colostomy patients have a temporary or permanent opening or stoma in the abdominal wall through which waste from the intestine is secreted. The waste, which may be fluid or semi-fluid, is periodically collected in a receptacle. It is necessary that the stoma be covered when the secretions are not being collected. This requires a bandage which has a high degree of absorbency and substantial ability to retain fluids.

High bulk is normally associated with bandages which have high absorbency and retention characteristics. However, in this case, bulk cannot be tolerated. Bandages used for this purpose must have minimum bulk so as not to be visible from outside of the patient's clothing.

Further, since the skin surrounding the stoma is very sensitive, particularly immediately after the operation, the bandage must be able to be applied and removed in a way that does not produce or contribute to skin irritation. At the same time, the bandage must be relatively secure with respect to the skin.

Many bandages employ materials which stretch in one direction so as to accommodate creasing of the skin so that no "channels" or spaces form between the bandage and the skin as the skin is flexed. However, materials which stretch in only one direction cannot prevent channeling when the skin is flexed in the other direction. It is therefore highly advantageous to have a bandage which is bdirectionally flexible so as to prevent channeling in both directions.

The present invention relates to a bandage with a unique construction which achieves the above functional requirements and at the same time can be manufactured relatively inexpensively using simple processing techniques.

It is, therefore, a prime object of the present invention to provide an improved bandage which has increased absorbency characteristics.

It is another object of the present invention to provide an improved bandage which has increased fluid retention abilities.

It is another object of the present invention to provide an improved bandage which prevents superabsorbent material from contacting the stoma.

It is another object of the present invention to provide an improved bandage which will prevent fluids from seeping out of the ends of the superabsorbent pad.

It is another object of the present invention to provide an improved bandage which will adhere to the skin as it is flexed, regardless of the direction of flexing.

It is another object of the present invention to provide an improved bandage which can be manufactured using simple processing techniques.

In accordance with the present invention, a bandage is provided with a base comprising a sheet of non-woven material and a layer of plastic. The base is coated, on its upper surface, with a layer of acrylic adhesive. A pad of superabsorbent material, smaller in size than the base, is wrapped in a sheet of non-woven wrapping material. The pad is affixed to the upper surface of the base by the acrylic adhesive layer. A portion of the acrylic adhesive layer forms a border around the superabsorbent pad.

The plastic layer may be a film bonded to the upper surface of the non-woven material. The film is preferably smaller in size than the non-woven material. A portion of the surface of the non-woven material is thus exposed. This exposed portion of the non-woven material is also coated with the adhesive.

However, in its most preferred form, the plastic layer is in the form of a plastic coating bonded to the lower surface of the non-woven material. Preferably, the coating and the non-woven material are substantially coextensive.

The non-woven material is preferably composed of polyester or polypropylene. The plastic layer is preferably composed of polyethylene.

To these and such other objects which may hereinafter appear the present invention relates to an improved bandage as described in the following specification and recited in the annexed claims taken together with the accompanying drawing where like numbers refer to like parts and in which:

FIG. 3 is a cross-sectional view of the preferred embodiment of the present invention taken along line 3—3 of FIG. 2;

FIG. 4 is an isometric view showing how the superabsorbent pad is wrapped;

FIG. 5 is an isometric view showing how the wrapped pad is sealed;

FIGS. 6 and 7 are end views of the superabsorbent pad showing how the wrapping material is folded;

FIG. 10 is a cross-sectional view taken along the line 10—10 of FIG. 9.

Figure 1:
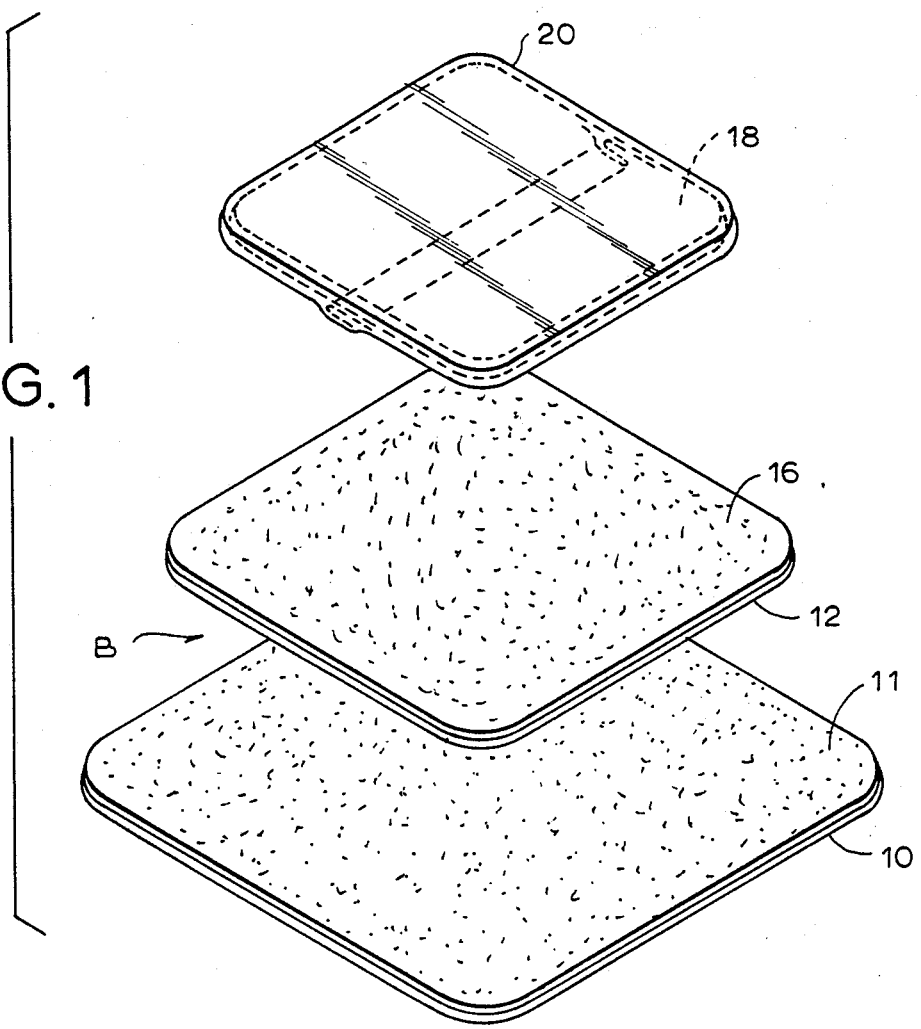
FIG. 1 is an exploded isometric view of a preferred embodiment of the bandage of the present invention.
Figure 2:
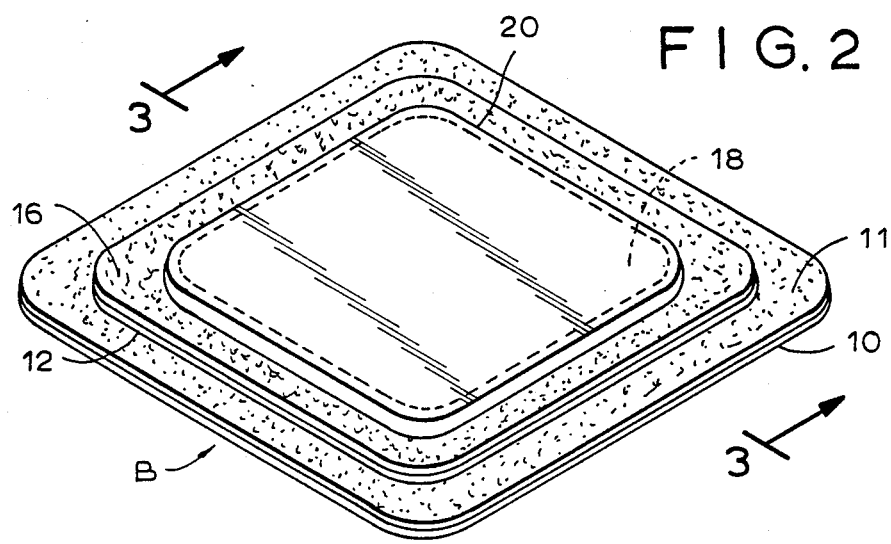
FIG. 2 is an isometric view of the bandage illustrated in FIG. 1.

As shown in FIGS. 1 and 2, the first preferred embodiment of the present invention comprises a substantially rectangular sheet of non-woven material 10 with rounded corners. Material 10 is preferably air-laid, wet-laid or spun-laid rayon, polyester or polypropylene having a basis weight of from 10 to 50 grams per square meter. Most preferably, polyester or polypropylene is used. This material is essentially non-absorbent and permits both air and liquid to pass therethrough. It also is extremely flexible.

Material 10 is coated with a layer of acrylic dermal adhesive 11 on its top surface. Adhesive 11 bonds the top surface of non-woven material 10 to a sheet of thin plastic film 12. Plastic film 12 also has rounded corners and may be composed of any suitable plastic, but is preferably a polyethylene sheet between 0.3 to 3 mils thick. Non-woven material 10 and plastic film 12 form the base, generally designated B, of the bandage.

The exposed surface of plastic film 12 is coated with an acrylic dermal adhesive 16 preferably of the same type as layer 11. This adhesive is gentle on the skin but will retain its adhesive properties even when wet.

A pad of superabsorbent material 18 is affixed to the base by layer 16. The term "superabsorbent" as used herein is intended to indicate any substance which can absorb more than its weight in liquid. The pad may be composed of multiple sheet layers, and consists of an air-laid composite of cellulose wood pulp fiber, polyethylene fibers and superabsorbent granules. One such material is commercially available from Dry Forming Processes of Orkelljunga, Sweden, under the tradename CELL-O-SOFT. This material, as illustrated in FIG. 4, is die cut into rectangular pads and then placed on a strip of non-woven material 20, similar to the material 10. Non-woven material 20 is then wrapped around the the superabsorbent pad 18, as seen in FIGS. 5, 6 and 7, such that the flaps 20a and 20b align and overlap and may be folded over in face-to-face relation as shown in FIG. 7. The ends of the unit are then crimped, cut and sealed along lines 22.

As shown in FIG. 1, the wrapped pad, with the flaps folded but not sealed, is placed in the center of the adhesive coated surface of the base B such that the wrapped pad adheres to the plastic film 12. The adhesive layer 16 maintains the unsealed flaps of the wrapping non-woven material 20 in the closed condition. The pad 18 is framed by a border of adhesive 11, 16 so as to adhere to the skin.

Figure 8:
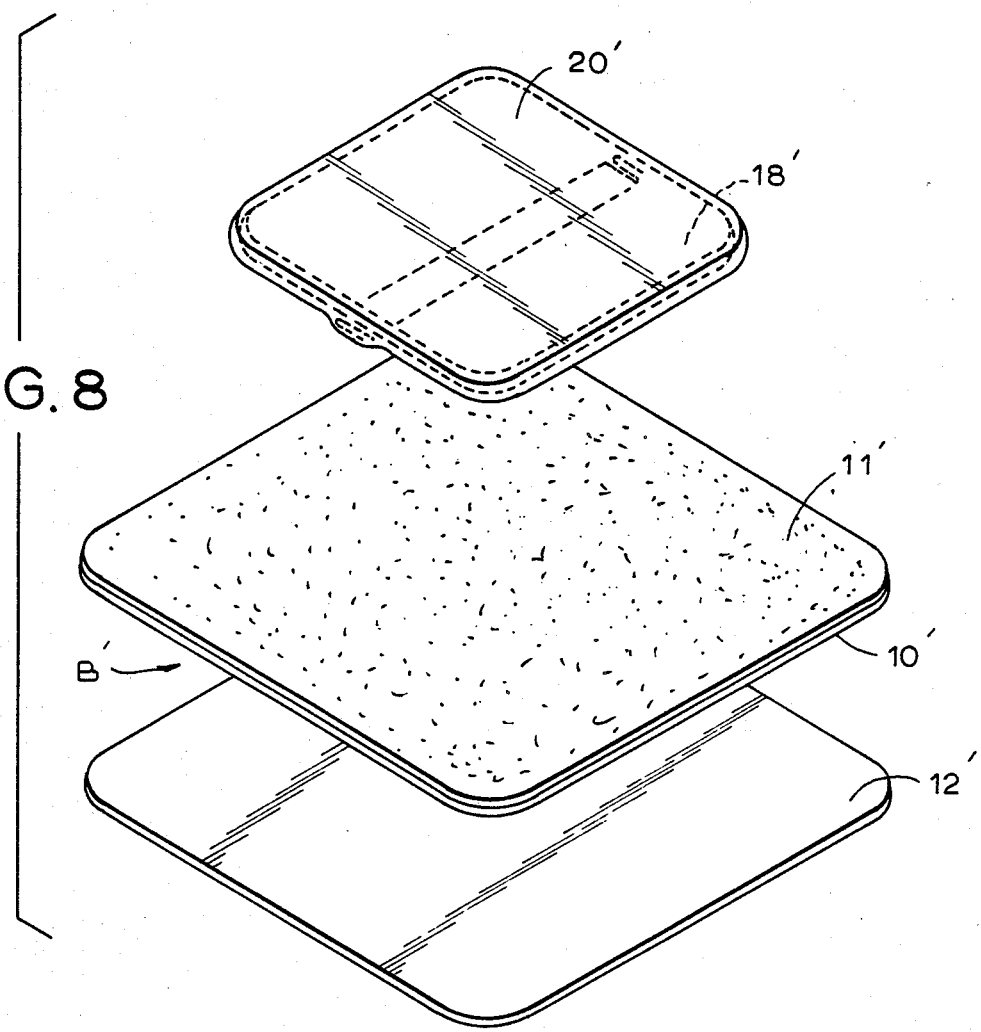
FIG. 8 is an exploded isometric view of the most preferred embodiment of the present invention.
Figure 9:
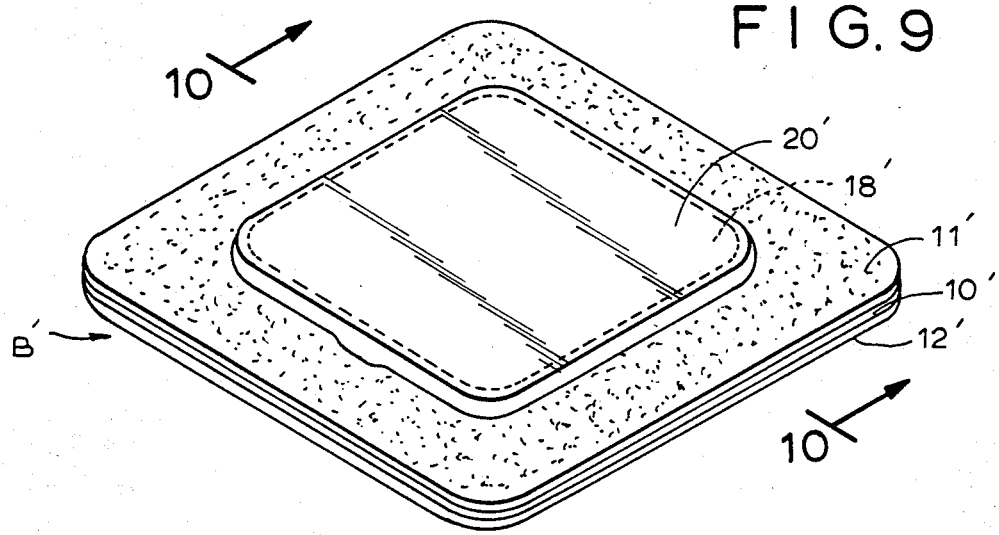
FIG. 9 is an isometric view of the bandage shown in FIG. 8.

The most preferred embodiment of the present invention is illustrated in FIGS. 8, 9 and 10. The most preferred embodiment of the present invention has corresponding elements to those described above with respect to the first preferred embodiment, shown in FIGS. 8, 9 and 10 with primes. The major difference between this embodiment and the embodiment shown in FIGS. 1 and 2 is the structure of base B. In this embodiment, base B is formed such that the plastic layer 12' is in the form of a plastic coating heat bonded to the bottom surface of material 10' and hence has the same length and width dimensions as the non-woven material 10' but is on the surface opposite to that to which pad 18' is affixed. Preferably, coating 12' is composed of a very thin layer of polyethylene.

Base B, which is a combination of non-woven material 10' and plastic coating 12' bonded together, can be manufactured and provided in rolls with the acrylic adhesive layer 11' already in place and covered by release paper. During the manufacturing process, the base material is cut to size and the wrapped superabsorbent pad placed thereon. Release paper is then placed over the interior surface to protect same.

Using a base layer consisting of a non-woven material with a plastic coating or film bonded thereto is advantageous because the non-woven material is bilaterally flexible and therefore will adhere to skin folds surrounding the stoma better than a plastic alone. However, the plastic layer 12' is required because it is water impervious and stretchable. The multilayer base material provides both properties.

The border of adhesive 11' surrounding the superabsorbent pad creates a fluid tight seal between the skin and the base B'. The seal extends around the pad 18' and prevents fluid from escaping from the sides of the pad 18'.

It should be noted that non-woven wrapping material is wrapped completely around superabsorbent pad so as to prevent any contact between the superabsorbent pad and the skin. Moreover, if any of the superabsorbent material crumbles, the wrapping will prevent same from spilling out of the bandage. Preferably, a relatively slow action superabsorbent material is employed. Such a material absorbs moisture slowly but is highly retentive.

A sheet of silicon release paper (not shown) can be used to cover the bandage so as to maintain the sterility thereof. The release paper is simply peeled from the bandage prior to application thereof to the skin, as is customary.

It should now be appreciated that the present invention relates to an improved bandage with a unique structure which results in a highly absorbent and retentive article in which the superabsorbent pad is isolated from the skin. The base has a multilayer structure which provides bidirectional flexibility to reduce channeling. The bandage includes a base including a non-woven material to which a plastic layer is bonded. The exposed top surface of the base is coated with an acrylic adhesive. A pad of superabsorbent material is wrapped in a non-woven material and sealed at its ends. The superabsorbent pad is then placed on the base and affixed thereto by the adhesive. The remaining exposed surface of the base, which is coated with the adhesive, forms a frame around the pad so as to adhere the bandage to the skin.

While only a limited number of preferred embodiments of the present invention have been disclosed for purposes of illustration, it is obvious that many modifications and variations could be made thereto. It is intended to cover all of these variations and modifications which would fall in the scope of the invention, as defined by the following claims:

I claim:

1. A bandage comprising a base which is comprised of a non-woven material and a plastic layer bonded to said non-woven material, a layer of acrylic adhesive on the body contacting surface of said plastic layer and a pad of superabsorbent material, smaller in size than said base, said superabsorbent pad being wrapped in a sheet of non-woven material and affixed to said body-contacting surface of said plastic layer by said adhesive layer, a portion of said adhesive layer forming a border around said pad and being adapted to adhere the bandage to the skin of the wearer.

2. The bandage of claim 1 wherein said plastic layer is a film and which further comprises a second acrylic adhesive layer on said non-woven material to bond said film to said non-woven material.

3. The bandage of claim 2 wherein said plastic film is smaller in size than said non-woven material so as to expose a portion of the surface of non-woven material with said second adhesive layer thereon.

4. The bandage of claim 1 wherein said non-woven material is composed of polypropylene.

5. The bandage of claim 1 wherein said plastic layer is composed of polyethylene.

* * * * *